United States Patent
Lott et al.

(10) Patent No.: US 8,153,106 B1
(45) Date of Patent: Apr. 10, 2012

(54) SILICONE BASED SUN SCREENING COMPOSITIONS WITH IMPROVED UVA1/UV RATIOS

(75) Inventors: Dennis Lee Lott, Flagler Beach, FL (US); Anthony J. O'Lenick, Jr., Dacula, GA (US)

(73) Assignee: Siltech Corporation, Toronto, Ontario (CA)

( * ) Notice: Subject to any disclaimer, the term of this patent is extended or adjusted under 35 U.S.C. 154(b) by 127 days.

(21) Appl. No.: 12/806,051

(22) Filed: Aug. 5, 2010

Related U.S. Application Data

(60) Provisional application No. 61/395,253, filed on May 12, 2010.

(51) Int. Cl.
- *A61K 8/00* (2006.01)
- *A61K 8/02* (2006.01)
- *C08G 77/04* (2006.01)

(52) U.S. Cl. .............................. 424/59; 424/401; 528/29

(58) Field of Classification Search ........................ None
See application file for complete search history.

(56) References Cited

U.S. PATENT DOCUMENTS

2009/0069466 A1   3/2009   Bonda

*Primary Examiner* — David J Blanchard
*Assistant Examiner* — Rachael E Bredefeld

(57) ABSTRACT

The present invention is directed to a synergistic blend of a sunscreen agent, specifically avobenzone and a specific class of ester that results in substantially improved sunscreen effectiveness, improving the performance of the sunscreen formulation as determined by the star system.

8 Claims, No Drawings

US 8,153,106 B1

SILICONE BASED SUN SCREENING COMPOSITIONS WITH IMPROVED UVA1/UV RATIOS

RELATED APPLICATION

This application claims priority to and benefit of U.S. Provisional Application No. 61/395,253 filed May 12, 2010, the disclosure of which is incorporated herein for all purposes.

FIELD OF THE INVENTION

The present invention is directed to a synergistic blend of a sunscreen agent and a specific silicones, herein referred to as avoboost silicones, that results in substantially improved sunscreen effectiveness, improving the performance of the sunscreen formulation as determined by the star system. Surprisingly it has been discovered that the compounds of this invention function as photostabilizers of Avobenzone.

BACKGROUND

UVA protection has been a source of increasing discussion worldwide due to the steadily climbing rates of skin cancer, and particularly malignant melanoma. There have been many who say one of the problems has been the emphasis on SPF, which have steadily increased, and not enough emphasis on UVA protection. The SPF test is a measurement of erythema and 85% to 90% of the erytema energy is UVB energy. While this means that to obtain SPFs higher than 10, some UVA protection must be present the SPF test provides little indication of the magnitude of the UVA protection. In fact, based on the 2007 FDA Sunscreen Monograph, Sunscreen Drug Products for Over-the-Counter Human Use; Proposed Amendment of Final Monograph; Proposed Rule, (2007 Monograph) the instruments utilized to test SPF may have as little as 9% of the erythemal energy coming from UVA and as little as 3% of the erythemal energy coming from UVAI energy. UVA energy is defined as the Ultraviolet energy from 320 nm to 400 nm and UVAI energy is defined as energy from 340 nm to 400 nm. There are several UVA tests that exist worldwide, but only since the 2007 Monograph has there been anything official in the US. The 2007 monograph lists two UVA tests that must be performed. One test, the JCIA Persistent Pigment Darkening test compares the amount of energy needed to produce melagenesis (tan) in unprotected skin versus the amount of energy needed to produce a tan in protected skin. This test predominantly is based on the amount of UV energy absorbed in the UVAII, 320 nm to 340 nm area of the Ultraviolet spectra. The FDA recognizing this devised a second test to measure the energy absorbed in the UVAI area of the spectra. Simply stated, this in vitro test is based on dividing the average amount of absorbance in the UVAI area by the average amount of absorbance in the entire UV spectra.

The resultant ratio determines the amount of UVA protection that can be labeled. Front panel labeling is required to reflect this by a star system and descriptor system as follows:

| UVAI/UV Ratio | Descriptor | No. of Stars |
| --- | --- | --- |
| <20 | No UVA claim | 0 |
| .20-.39 | Low UVA | 1 |
| .40-.69 | Medium | 2 |
| .70-.95 | High | 3 |
| >0.95 | Highest | 4 |

To obtain the desired ratio, product absorbance must have increasing magnitude of absorbance in the UVA region and increasing breadth in the longer UVAI wavelengths. To obtain the highest rating the product needs to absorb as much in the long UVAI wavelengths as is absorbed in the shorter wavelengths. While this sounds simple in theory, it is very contradictory to common sunscreen products in the US as well as the world, which almost always have the predominant amount of their absorbance in the UVB region and then rapidly taper off in the UVAII and UVAI. Obtaining the highest ratio with an SPF of 30 or higher is practically impossible with existing US approved sunscreen active materials without using a product so opaque that few if any would use.

The only chemical sunscreen available to use in the US that absorbs with any significance in the UVAI region is Butyl Methoxydibenzoylmethane, more commonly known as Avobenzone. And even Avobenzone is woefully lacking in producing the broad coverage needed to obtain a 4 star, high SPF product since the maximum absorbance of Avobenzone in a polar solvent such as ethanol is 357 nm and the absorbance drops off extremely fast at increasingly higher wavelengths. The maximum absorbance is even lower in non-polar solvents such as most oils. This situation is exacerbated by the fact that once an alcohol product is applied to the skin the alcohol quickly evaporates leaving the Avobenzone in an increasingly polar environment. Further to that most sunscreen products are in fact emulsions that have the Avobenzone dissolved in a non-polar oil phase in order for it to be solubilized and emulsified. The maximum absorbance in some commonly used oil ingredients used to solubilize and emulsify Avobenzone have in fact much lower maximum absorptions. For example Avobenzone maximum absorbance in Mineral Oil is only at 351 nm and C12-15 Alkyls Benzoate is at 355 nm. Note a typical absorption pattern for Avobenzone in C12-15 alkyl benzoate, run using a UV-Visible spectrophotometer results in a spectrum with very little absorbance in the range of 390 nm. Improving the absorbance at this wavelength would result in an improved star rating.

It is known in the art that light radiation of wavelengths of from 290 to 320 nm, i.e., UV-B irradiation, causes skin burning and erythema. For these reasons, as well as for aesthetic reasons, there is an increasing demand for means of controlling this natural tanning in order to thereby control the color of the skin. This UV-B radiation must thus be screened from the skin."

It is also known to this art that UV-A radiation, of wavelengths of from 320 to 400 nm, which tan the skin, also adversely affects it, especially in the case of sensitive skin or skin which is continually exposed to solar radiation. UV-A rays especially cause a loss in the elasticity of the skin and the appearance of wrinkles, promoting premature skin aging. Such irradiation promotes triggering of the erythemal reaction or amplifies this reaction in certain individuals and may even be the source of phototoxic or photoallergic reactions. Thus, for aesthetic and cosmetic reasons, such as conservation of the natural elasticity of the skin, for example, an ever-increasing number of individuals wish to control the effect of UV-A rays on their skin, it is desirable to also screen out UV-A radiation.

A wide variety of compounds suited for photoprotection (UV-A and/or UV-B) of the skin are known to this art. Most of these are aromatic compounds exhibiting absorption of UV radiation in the region from 280 to 315 nm, or in the region from 315 to 400 nm, or in both of these regions. There is no good way known at present to modify the absorption properties of molecules to meet the specific needs, or to combine products to cover a wide range of UV wavelengths. Products heretofore known are typically formulated into antisun or sunscreen compositions which are in the form of an emulsion of oil-in-water type or water in oil type, and which thus contain, in various concentrations, one or more conventional lipophilic and/or hydrophilic organic screening agents. These are capable of selectively absorbing harmful UV radiation of specific wavelength, depending upon structure of such screening agents (and their amounts) being selected as a function of the desired sun protection factor SPF (the sun protection factor being expressed mathematically by the ratio of the irradiation time required to attain the erythema-forming threshold with the UV screening agent to the time required to attain the erythema-forming threshold in the absence of UV screening agent).

It is a long felt need to have a sunscreening agent that can absorb ultra violet radiation at specific desired wavelengths. In addition, these compounds exhibiting anti-UV activity must also have good cosmetic properties in compositions comprised thereof, good solubility in the usual solvents, and in particular fatty substances such as oils and greases, as well as good resistance to water and to perspiration.

U.S. Pat. No. 6,080,880 issued Jun. 27, 2000 teaches that grafting at least one cinnamamide, benzalmalonamide or benzalmalonate group onto a short-chain silicone molecule, in particular onto a linear silicone chain comprising not more than six Si atoms, novel compounds are obtained which obviate the drawbacks of the screening agents of the prior art, these novel compounds having, other than very high-performance screening properties, very good solubility in the usual organic solvents and in particular fatty substances such as oils, as well as excellent cosmetic properties, which render them particularly suitable for use as sunscreens in, or for the formulation of, cosmetic compositions suited for protecting the skin and/or the hair against the deleterious effects of ultraviolet radiation. The teachings state "And, taking account of their relatively small size, these novel compounds are easier to synthesize".

U.S. Pat. No. 6,346,595 issued Feb. 12, 2002 to O'Lenick, incorporated herein by reference, teaches "A major object of the present invention is the provision of novel silicone compounds that contain a UV-absorber and a polar alkoxylated group. The presence of the polar alkoxylated group not only has a dramatic effect upon solubility of the sunscreen, but also shifts the UV absorption properties, making it possible to synthesize products that have a specified UV absorption property. Since UV-B is the major area that causes problems with sun tanning, the products can be customized to have the desired water or oil solubility as well as the desired UV spectra. These novel compounds can be prepared to have the desired spectra, in addition to very good solubility in fatty materials, or aqueous systems, improved cosmetic properties, and which otherwise avoid those disadvantages and drawbacks to date characterizing the state of this art." While interesting the approach is to make a molecule with a modified UV spectra. This approach results in new heretofore-unknown UV molecules. We have surprisingly discovered that by picking the proper molecule we can modify the UV spectra of avobenzone, a well-known sunscreen agent and modify it to give wider more efficient sun protection.

THE INVENTION

Object of the Invention

It is the object of the present invention to provide improved sunscreen compositions. Specifically the incorporation of the compositions of the present invention in place of simply using avobenzone results in improved star rating.

An additional aspect of the present invention is to provide a class of silicones that interacts with the avobenzone to not only shift the absorbance to higher wavelengths, but to do so in a way that the greater percentage of the absorbance in the higher region. Without wanting to be bound to a specific theory of why the compounds of the present invention work, the molecules interact with avobenzone to stabilize the molecule, altering the critical keto/enol ratio.

Another aspect of the present invention is to provide a series products differing in polarity that provide the desired improvements in the shifting of both the wavelength and the shifting of the percentage of the absorbance at the higher wavelength. This results in synergistic products that interact with avobenzone providing the desired effects upon the sunscreening properties, AND also allow for the preparation of synergistic blends with avobenzone that range from oil soluble to water soluble. This aspect is a very unappreciated advantage since it allows the formulator to make products that range from alcohol based sunscreens to oil based sunscreens, and even hydroalcoholic products that are easy to use and not flammable.

SUMMARY OF THE INVENTION

The present invention describes compositions comprising a specific Avo-boosting silicone and avobenzone. The selection of the proper ester results in improved star system rating.

DETAILED DESCRIPTION OF THE INVENTION

The present invention is directed to an improved sunscreen composition, which comprises (1) a silicone compound conforming to the following structure

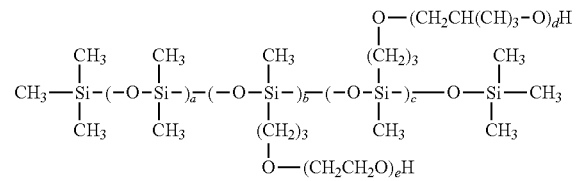

wherein;

a is an integer ranging from 0 to 50;

b is an integer ranging from 1 to 20;

c is an integer ranging from 1 to 20;

d is an integer ranging from 5 to 20;

e is an integer ranging from 5 to 20;

and (2) avobenzone.

Another aspect of the present invention is directed to an a process for providing improved sun protection, which comprises contacting the skin with an effective sun screening concentration of a composition comprising:

(1) a silicone compound conforming to the following structure

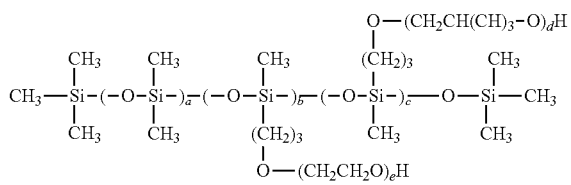

wherein;
a is an integer ranging from 0 to 50;
b is an integer ranging from 1 to 20;
c is an integer ranging from 1 to 20;
d is an integer ranging from 5 to 20;
e is an integer ranging from 5 to 20;
and
(2) avobenzone.

The effective sun screening concentration of the composition of the present invention ranges from 1 percent to 50 percent of the composition by weight.

In a preferred embodiment the effective sun screening concentration of the composition of the present invention ranges from 10 percent to 20 percent of the composition by weight.

PREFERRED EMBODIMENTS

In a preferred embodiment the ratio of ester to avobenzone ranges from 50:1 to 1:1.

In a preferred embodiment the ratio of ester to avobenzone ranges from 3:1 to 1:1.

In a preferred embodiment a ranges from 2 to 50.

In a preferred embodiment the ratio of b:c ranges from 10:1 to 1:10.

In a preferred embodiment the ratio of b:c ranges from 10:1 to 1:1.

In a preferred embodiment the ratio of b:c ranges from 1:5 to 1:10

We have surprisingly found that compounds conforming to the above structure stabilize avobenzone, shift the absorbance maximum to higher values and provide higher star ratings that formulations lacking these additives do not have.

In addition the ability to alter solubility of these polar materials in solvents is a key aspect of the invention. The compounds of the present invention contain both polyoxyethylene and polyoxypropylene groups. The former water soluble and the latter water insoluble. The key to the invention which has been an unappreciated advantage is that polyoxypropylene groups while water insoluble are polar and can effect interaction with avobenzone, improving both the lambda max and the star rating. Materials with just polyoxyethylene groups are too polar to solubilize avobenzone.

In order to evaluate the effectiveness of the compounds of the present invention we looked at the maximum absorbance and the % absorbance at 390 nm.

The method was as follows:
All absorbance's were determined by spreading a thin film on Polymethylmethacrylate; Plexiglass (PMMA) plates and scanning on an Optimetrics SPF 290 spectrophotometer from 290 nm to 400 nm. Each sample was scanned 4 times and absorbances averaged at 1 nanometer increments. The wavelength at which maximum absorbance occurred was noted. To study the breadth of the absorbance at the long wavelength areas of the UVA spectra, the absorbance at 380 and 390 was converted to a percentage of the maximum absorbance as follows:

($Abs$ at 380×100)/Max $Abs$=% $Abs$@380

($Abs$ at 390×100)/Max $Abs$=% $Abs$@390

Evaluating the % of absorbance at 390 is an indication of how well the synergistic blend will boost the star rating. Simply stated, the more absorbance in the higher wavelengths, the higher the UVA and the higher the star rating.

PRIOR ART COMPOUNDS

Example 1

Mineral Oil

Mineral Oil is an item of commerce available from a variety of sources. Mineral oil or liquid petroleum is a by-product in the distillation of petroleum to produce gasoline and other petroleum based products from crude oil. It is a transparent, colorless oil composed mainly of alkanes (typically 15 to 40 carbons) and cyclic paraffins, related to petroleum jelly (also known as "white petrolatum"). It has a density of around 0.8 g/cm$^3$ Mineral oil is a common ingredient in sun care products, baby lotions, cold creams, ointments and cosmetics.

Example 2

Octyl Palmitate

Octyl palmitate is the ester of 2-ethylhexanol and palmitic acid and item of commerce available from a variety of vendors. It is commonly used in sun care products and has a CAS Registry Number: 29806-73-3

Example 3

C12-15 Benzoate

Alkyl (C12-15) Benzoate consists of esters of a mixture of C12 to C15 primary and branched alcohols (Neodol 25) and benzoic acid. It is an item of commerce available from a variety of sources. It is commonly used in sun care products and has a CAS Registry Number: 68411-27-8

Raw Material Examples

The raw materials useful to make the compounds of the present invention conform to the following structure are commercially available from Siltech LLC and conform to the following structure:

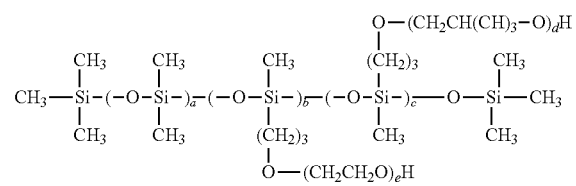

wherein;
a is an integer ranging from 0 to 50;
b is an integer ranging from 1 to 20;
c is an integer ranging from 1 to 20;
d is an integer ranging from 5 to 20;
e is an integer ranging from 5 to 20;

| Example | a | b | c | d | e |
|---------|----|----|----|----|----|
| 4 | 20 | 8 | 2 | 9 | 9 |
| 5 | 20 | 6 | 4 | 9 | 9 |
| 6 | 20 | 4 | 6 | 9 | 9 |
| 7 | 20 | 2 | 8 | 9 | 9 |
| 8 | 0 | 10 | 10 | 20 | 20 |
| 9 | 50 | 1 | 20 | 10 | 10 |
| 10 | 25 | 20 | 20 | 20 | 20 |

Evaluation of Avobenzone in Several Solvents
Avobenzone

Avobenzone is an item of commerce, sold under the trade names Parsol 1789, Eusolex 9020, Escalol 517. The INCI name is Butyl Methoxydibenzoylmethane. It is an oil soluble ingredient used in sunscreen products to absorb the full spectrum of UVA rays. It is a dibenzoylmethane derivative. Avobenzone exists in the ground state as a mixture of the enol and keto forms, favoring the chelated enol. Its ability to absorb ultraviolet light over a wider range of wavelengths than many organic sunscreen agents has led to its use in many commercial preparations marketed as "broad spectrum" sunscreens. Avobenzone has an absorption maximum of 357 nm. The IUPAC name is 1-(4-Methoxyphenyl)-3-(4-tert-butylphenyl)propane-1,3-dione.

In order to evaluate the effect of various solvents on the absorption maximum of Avobenzone the material was added to various oil phases used in the cosmetic industry at 3% and the wavelength evaluated.

| Standard Materials | Max Absorbance | % abs @ 390 |
|---|---|---|
| Example 1 Mineral Oil | 351 | 7.8 |
| Example 2 Octyl Palmitate | 351 | 10 |
| Example 3 C12-15 Alkyl Benzoate | 355 | 16.1 |

| Products of the Invention | Max Absorbance | % abs @ 390 |
|---|---|---|
| Example 4 | 357 | 28.3 |
| Example 5 | 358 | 26.8 |
| Example 6 | 356 | 28.8 |
| Example 7 | 356 | 22.1 |
| Example 8 | 357 | 27.1 |
| Example 9 | 357 | 29.4 |
| Example 10 | 356 | 28.6 |

Standard cosmetic oil phases lower the lambda max, and have a negative effect upon star rating. The compounds of the present invention shift the wavelength of maximum absorption of avobenzone up and provide the sunscreen efficiency increase desired.

In working with UV absorbers, the wavelength and the amplitude of the response are both critical to performance.

The lambda max is the wavelength of maximum absorption. We have discovered a way of making a product that provides UV protection at a higher improved wavelength based upon interaction of the active with the compounds of the present invention. The result is a more effective sunscreen as shown by the star rating system.

The ability to both shift the lambda max and the amplitude of the avobenzone makes the compound of the present invention uniquely of interest in the formulation of sunscreening materials that use approved sunscreens (as required by U.S. law, and provide the highest star rating possible.

The importance of this surprising discovery is it now means more UVB sunscreen can be added to a formulation while maintaining a UVA/UV ratio. Thus it becomes possible to increase the SPF while still maintaining the desired ratio. Formulation 1 is a very good 3 star (high UVA) rated formula having an SPF of approximately 40 and a ratio of 0.946, just missing the 5 star highest category. In formula 2, by significantly reducing the strongest absorbing UVB sunscreen, Octocrylene (OCR), to 3.4% from 4.0% a 4 star 0.956 ratio was obtained. Formula 3, an example of this invention by contrast has an identical ratio, 0.956 (4 star highest) ratio but yet has OCR increased to 4.2%. This surprising discovery means that SPFs can be dramatically increased while still maintaining the highest ratio of UVA protection. Formulation 2 was in vivo SPF tested and yielded a result of 38. According to BEERS Law absorbance is directly related to concentration, thus the SPF of Formula 3 will increase dramatically over Formula 2 and 1. If the SPF of Formula 2 is 40 it is conceivable that the SPF of Formula 3, an example of this invention, would be far in excess of SPF 50. Thus the example of the invention, Formula 3 would not only be labeled as the highest UVA but highest UVB allowed by the FDA in the 2007 monograph.

Formulation Example

| | Formula 1 | Formula 2 | Formula 3 |
|---|---|---|---|
| Compound 5 | | | 8.0% |
| Compound 1 | 8.0% | 8.0% | |
| Avobenzone | 3.0% | 3.0% | 3.0% |
| Octocrylene | 4.0% | 3.4% | 4.2% |
| Homosalate | 2.0% | 2.0% | 2.0% |

All percents are wt/wt.

Evaluation of Performance

| | SPF | Star Rating |
|---|---|---|
| Formulation 1 | 43 | 3 |
| Formulation 2 | 39 | 4 |
| Formulation 3 | 48 | 4 |

The use of compound 5 (compound of the present invention) results in a formulation having 4 stars and a 50 SPF. Formula 2 had a much lower SPF, whilst formula 1 had both a low spf and star rating. Clearly Formulation 3 (containing a compound of the present invention) has the best heretofore not attainable performance.

The example above in no way restricts the use of the compounds of the current invention together with avobenzone in conjunction with other ingredients. It is obvious that anyone skilled in the art would realize that there exists many other combinations of sunscreens that can be utilized. Likewise it is obvious that anyone skilled in the art could utilize a wide variety of additives, such as emollients, emulsifiers, antioxidants, preservatives, fragrances, etc. Sunscreens actives could be chosen from, but not limited to a list that includes PABA, Cinoxate, Dioxybenzone, Homosalate, Menthyl Anthranilate, Octocrylene, Oxybenzone, Octisalate, Padimate O, Phenylbenzimidazole Sulfonic Acid, Sulsiobenzone, Titanium dioxide, Zinc Oxide. Additionally, anyone skilled in the art would be cognizant that many ingredients frequently utilized in sunscreen formulations that although not considered active ingredients, are represented as boosting SPF or photostabilizing, could be utilized in combinations with the compounds of this invention.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A sunscreen composition, which comprises:
   (1) a silicone compound conforming to the following structure

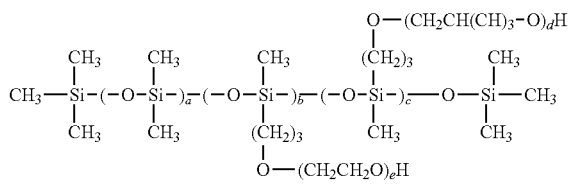

wherein;
   a is an integer ranging from 0 to 50;
   b is an integer ranging from 1 to 20;
   c is an integer ranging from 1 to 20;
   d is an integer ranging from 5 to 20;
   e is an integer ranging from 5 to 20;
   and
   (2) avobenzone.

2. A sunscreen composition of claim 1 wherein a ranges from 7 to 9.

3. A sunscreen composition of claim 1 wherein a ranges from 8 to 10.

4. A process for providing improved sun protection, which comprises
   contacting the skin with an effective sun screening concentration of a composition comprising:
   (1)) a silicone compound conforming to the following structure

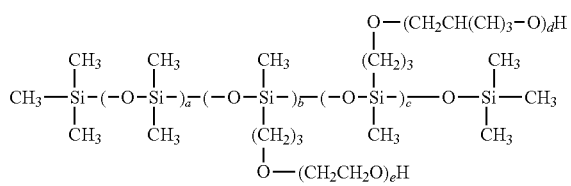

wherein;
   a is an integer ranging from 0 to 50;
   b is an integer ranging from 1 to 20;
   c is an integer ranging from 1 to 20;
   d is an integer ranging from 5 to 20;
   e is an integer ranging from 5 to 20;
   and
   (2) avobenzone.

5. A process of claim 4 wherein the effective sun screening concentration of the composition of the present invention ranges from 1 percent to 20 percent of the composition by weight.

6. A process of claim 4 wherein the effective sun screening concentration of the composition of the present invention ranges from 10 percent to 20 percent of the composition by weight.

7. A process of claim 4 wherein a ranges from 7 to 9.

8. A process of claim 4 wherein a ranges from 8 to 10.

* * * * *